US012775002B2

(12) United States Patent
Inaba et al.

(10) Patent No.: US 12,775,002 B2
(45) Date of Patent: Oct. 27, 2026

(54) GREASE DETERIORATION DETECTING METHOD AND LUBRICANT DETERIORATION DETECTING METHOD

(71) Applicant: NSK LTD., Tokyo (JP)

(72) Inventors: Takenobu Inaba, Fujisawa (JP); Keisuke Yokoyama, Fujisawa (JP); Shunsuke Iwase, Fujisawa (JP)

(73) Assignee: NSK LTD., Tokyo (JP)

( * ) Notice: Subject to any disclaimer, the term of this patent is extended or adjusted under 35 U.S.C. 154(b) by 253 days.

(21) Appl. No.: 18/565,298

(22) PCT Filed: Jun. 2, 2022

(86) PCT No.: PCT/JP2022/022564
§ 371 (c)(1),
(2) Date: Nov. 29, 2023

(87) PCT Pub. No.: WO2022/255472
PCT Pub. Date: Dec. 8, 2022

(65) Prior Publication Data

US 2024/0310354 A1 Sep. 19, 2024

(30) Foreign Application Priority Data

Jun. 3, 2021 (JP) ................................ 2021-093548
Feb. 21, 2022 (JP) ................................ 2022-025090
(Continued)

(51) Int. Cl.
*G01N 33/28* (2006.01)
*G01N 1/38* (2006.01)
(Continued)

(52) U.S. Cl.
CPC .......... *G01N 33/2888* (2013.01); *G01N 1/38* (2013.01); *G01N 21/255* (2013.01);
(Continued)

(58) Field of Classification Search
CPC .... G01N 33/2888; G01N 1/38; G01N 21/255; G01N 21/8422; G01N 21/94;
(Continued)

(56) References Cited

U.S. PATENT DOCUMENTS

2012/0086942 A1* 4/2012 Honda .................. G01N 21/31 356/436
2016/0018336 A1* 1/2016 Schornstein .......... G01N 31/22 436/139
(Continued)

FOREIGN PATENT DOCUMENTS

JP 3-167414 A 7/1991
JP 8-278112 A 10/1996
(Continued)

OTHER PUBLICATIONS

English Translation of Cosmo JP-H09236593-A Description (Year: 1997).*
(Continued)

*Primary Examiner* — Tarifur R Chowdhury
*Assistant Examiner* — Akbar H. Rizvi
(74) *Attorney, Agent, or Firm* — Sughrue Mion, PLLC

(57) ABSTRACT

Provided is a grease deterioration detecting method which can detect deterioration of grease and in which the amount of grease necessary for detecting deterioration is small. The grease deterioration detecting method includes a dilution step of diluting grease with a diluent to obtain diluted grease, and a measurement step of measuring a color of the diluted grease with a sensor.

20 Claims, 3 Drawing Sheets

(30) Foreign Application Priority Data

Mar. 4, 2022 (JP) .............................. 2022-004481D
May 27, 2022 (JP) ................................ 2022-086825

(51) Int. Cl.
*G01N 21/25* (2006.01)
*G06T 7/00* (2017.01)
*G06T 7/90* (2017.01)

(52) U.S. Cl.
CPC .............. *G06T 7/0002* (2013.01); *G06T 7/90* (2017.01); *G06T 2207/10024* (2013.01)

(58) Field of Classification Search
CPC ............ G01N 2201/121; G01N 21/251; G06T 7/0002; G06T 7/90; G06T 2207/10024; G01J 3/50; G01J 3/52
See application file for complete search history.

(56) References Cited

U.S. PATENT DOCUMENTS

| | | | | |
|---|---|---|---|---|
| 2016/0025619 | A1* | 1/2016 | Katsaros | F16C 19/525 384/448 |
| 2016/0252448 | A1* | 9/2016 | Ida | G01N 21/255 356/70 |
| 2017/0318192 | A1* | 11/2017 | Ogatsu | H04N 1/6008 |
| 2018/0038417 | A1* | 2/2018 | Lang | F16C 41/008 |
| 2019/0086382 | A1* | 3/2019 | Inaba | G01N 33/2888 |
| 2019/0086383 | A1 | 3/2019 | Vann et al. | |
| 2021/0139040 | A1* | 5/2021 | Ganiger | G06N 20/00 |
| 2022/0156909 | A1* | 5/2022 | Sekiguchi | G01J 3/2823 |

FOREIGN PATENT DOCUMENTS

| | | | | | |
|---|---|---|---|---|---|
| JP | 9-236593 | A | | 9/1997 | |
| JP | H09236593 | A | * | 9/1997 | |
| JP | 11-201729 | A | | 7/1999 | |
| JP | 2000-131616 | A | | 5/2000 | |
| JP | 2002-106785 | A | | 4/2002 | |
| JP | 5188088 | B2 | | 4/2013 | |
| JP | 2014-085193 | A | | 5/2014 | |
| JP | 5843223 | B2 | * | 1/2016 | |
| JP | 5980591 | B2 | | 8/2016 | |
| JP | 2017-181036 | A | | 10/2017 | |
| WO | WO-2010021283 | A1 | * | 2/2010 | G01N 33/2888 |
| WO | WO-2014192912 | A1 | * | 12/2014 | G01N 21/251 |
| WO | 2019/193247 | A1 | | 10/2019 | |
| WO | 2020/203995 | A1 | | 10/2020 | |

OTHER PUBLICATIONS

English Translation of Onuma et al.WO-2014192912-A1 Description (Year: 2014).*

English Translation of Tatsuoka et al JP-5843223-B2 Description (Year: 2016).*

English Translation of Endo et al WO-2010021283-A1 Description (Year: 2010).*

Communication issued on Sep. 4, 2024 by the European Patent Office for European Patent Application No. 22816217.8.

Communication issued on Nov. 27, 2024 by the European Patent Office for European Patent Application No. 22816217.8.

International Search Report (PCT/ISA/210) issued on Aug. 23, 2022 by the International Searching Authority in International Patent Application No. PCT/JP2022/022565.

Written Opinion (PCT/ISA/237) issued on Aug. 23, 2022 by the International Searching Authority in International Patent Application No. PCT/JP2022/022565.

Office Action issued on Oct. 7, 2025 by the Japanese Patent Office in corresponding JP Patent Application No. 2022-004481.

* cited by examiner

GREASE DETERIORATION DETECTING METHOD AND LUBRICANT DETERIORATION DETECTING METHOD

CROSS-REFERENCE TO RELATED APPLICATIONS

This application is a National Phase Entry of PCT International Application No. PCT/JP2022/022564, filed on Jun. 2, 2022, which claims priority to Japanese Patent Application No. 2021-093548 filed on Jun. 3, 2021, Japanese Patent Application No. 2022-025090 filed on Feb. 21, 2022, Japanese Design Registration Application No. 2022-004481 filed on Mar. 4, 2022, and Japanese Patent Application No. 2022-086825 filed on May 27, 2022, the contents of all of which are incorporated herein by reference in their entirety.

TECHNICAL FIELD

The present invention relates to a method for detecting a deterioration state of grease and a method for detecting a deterioration state of a lubricant.

BACKGROUND ART

First Problem of Present Invention

Patent Literature 1 discloses a failure prediction device that predicts a failure of a rolling bearing by measuring a concentration of iron powder in lubricating grease used for the rolling bearing from a loss of a magnetic balance between an excitation coil and a detection coil.

However, the technique disclosed in Patent Literature 1 has a problem that the amount of grease necessary for measuring the concentration of the iron powder is relatively large. In addition, the technique disclosed in Patent Literature 1 cannot detect oxidative deterioration of grease.

Second Problem of Present Invention

In addition, grease is used for components of various mechanical devices including a rolling bearing and a speed reducer. Abnormal wear is a cause of a failure of the components. However, when abnormal wear occurs, the grease is contaminated by foreign matters such as iron powder, and the grease deteriorates. Further, there are some factors in deterioration of grease, such as deterioration of grease caused by changes in components caused by application of heat and deterioration of grease due to oxidation.

Regarding lubricating oil used for the same purpose as grease, various methods for detecting a state such as deterioration have been studied. For example, Patent Literature 2 discloses a color sensor attached to a mechanical device, and a state of the lubricating oil can be detected by the color sensor.

However, it is difficult to analyze the deterioration of grease because grease has low fluidity and low light transmittance compared with the lubricating oil.

The deterioration of grease is limited to the contamination by iron powder. For example, Patent Literature 1 discloses a failure prediction device that predicts a failure of a measurement target component by measuring a concentration of iron powder in lubricating grease used for the measurement target component from a loss of a magnetic balance between an excitation coil and a detection coil.

However, the technique disclosed in Patent Literature 1 requires a relatively large amount of grease to measure the concentration of the iron powder. In addition, it is necessary to install a sensor part of the failure prediction device at a position to be detected, and it takes time and costs from the manufacture of the device to the installation and prediction. Furthermore, it is not possible to detect deterioration caused by changes in components due to oxidation or heat of grease, which is limited to detection of deterioration caused by contamination of grease by iron powder.

Third Problem of Present Invention

A lubricant used for lubrication of various mechanical devices is oxidized in use, or is deteriorated over time due to foreign matter contamination.

As a method for detecting the deterioration state of the lubricant, for example, Patent Literature 2 describes a sensor that detects a deterioration state of a lubricant from a light transmission state by causing the lubricant to enter a gap formed between a light emitting element (white LED) and a light receiving element (RGB sensor).

However, in the method for detecting the deterioration state of the lubricant described in Patent Literature 2, a relatively large amount of lubricant is required, and only the lubricating oil can be measured, and for example, grease cannot be detected. In addition, there is a problem of deterioration of the sensor caused by immersing the sensor in the lubricant, and it is necessary to clean the sensor. Furthermore, the type of the light source is limited to the white LED, and the detection place is restricted.

CITATION LIST

Patent Literature

Patent Literature 1: Japanese Patent No. 5188088
Patent Literature 2: Japanese Patent No. 5980591

SUMMARY OF INVENTION

Technical Problem

In view of the first problem of the present invention, it is a first object of the present invention to provide a grease deterioration detecting method which can detect deterioration of grease and in which the amount of grease necessary for detecting deterioration is small.

In view of the second problem of the present invention, it is a second object of the present invention to provide a grease deterioration detecting method, which can detect deterioration caused by oxidation or heat in a short time with a small amount of grease in addition to deterioration caused by contamination by foreign matters such as iron powder.

In view of the third problem of the present invention, it is a third object of the present invention to provide a method for detecting grease as a lubricant in addition to lubricating oil, which can easily and more accurately detect the deterioration state of the lubricant in a short time without requiring deterioration or cleaning of the detection device with a small amount of grease, and can detect the deterioration state of the lubricant in various places without limitation on the type of the light source.

Solution to Problem

The first object of the present invention is achieved by the configuration of the following [1] according to the grease deterioration detecting method.

[1] A grease deterioration detecting method, which is a method for detecting deterioration of grease, the method including:

a dilution step of diluting grease with a diluent to obtain diluted grease; and a measurement step of measuring a color of the diluted grease with a sensor.

A preferred embodiment of the present invention relating to the grease deterioration detecting method relates to the following [2] to [4].

[2] The grease deterioration detecting method according to [1], in which the sensor is a color sensor.

[3] The grease deterioration detecting method according to [1] or [2], in which the diluent is an organic solvent.

[4] The grease deterioration detecting method according to [3], in which the organic solvent is at least one selected from the group consisting of n-hexane, kerosene, and gasoline.

In this description, the inventions relating to the above [1] to [4] are referred to as a "first invention group".

The second object of the present invention is achieved by the following configuration [5] relating to the grease deterioration detecting method.

[5] A grease deterioration detecting method, which is a method for detecting deterioration of grease, the method comprising:

a step of forming a thin film by sandwiching grease between a pair of plates made of a transparent material and spreading the grease; and a step of measuring a color of the thin-film grease with a camera or a sensor, in which a degree of deterioration of the grease is determined by the measurement.

Further, a preferred embodiment of the present invention relating to the grease deterioration detecting method relates to the following [6] and [7].

[6] The grease deterioration detecting method according to [5], in which the sensor is a color sensor.

[7] The grease deterioration detecting method according to [5] or [6], in which the transparent material is at least one selected from the group consisting of glass, acryl, polyethylene terephthalate, and polycarbonate.

In this description, the inventions relating to the above [5] to [7] are referred to as a "second invention group".

The third object of the present invention is achieved by the following configuration [8] relating to the lubricant deterioration detecting method.

[8] A lubricant deterioration detecting method including:

a step of imaging only a lubricant or the lubricant diluted with a solvent together with a color chart using an imaging device; and a step of determining a deterioration state of the lubricant from image information of only the imaged lubricant or the imaged lubricant diluted with the solvent based on image information of the imaged color chart.

A preferred embodiment of the present invention relating to the lubricant deterioration detecting method relates to the following [9] to [13].

[9] The lubricant deterioration detecting method according to [8], in which white balance of the image information of only the imaged lubricant or the imaged lubricant diluted with the solvent is corrected based on white balance of the image information of the color chart, and a deterioration state of the lubricant is determined based on the corrected image information.

[10] The lubricant deterioration detecting method according to [8] or [9], in which the imaging device has a white balance correction function.

[11] The lubricant deterioration detecting method according to [10], in which the imaging device is a digital camera or a camera-equipped portable terminal.

[12] The lubricant deterioration detecting method according to [8] or [9], in which the lubricant is lubricating oil or grease.

[13] The lubricant deterioration detecting method according to [8] or [9], in which the solvent contains an organic solvent, a kerosene compound, or a gasoline compound.

In this description, the inventions relating to the above [8] to [13] are referred to as a "third invention group".

Advantageous Effects of Invention

According to the present invention relating to the "first invention group", deterioration of grease can be detected with a small amount of grease.

According to the present invention relating to the "second invention group", not only the contamination by foreign matters such as iron powder but also the deterioration of grease caused by oxidation or heat can be detected. In addition, since deterioration can be detected in a short time from a small amount of grease, it is very useful in terms of cost and time, and in addition, by collecting grease at a plurality of any positions of a component, a position where the grease deteriorates may also be known at a pin point and a degree of deterioration may also be known on the spot.

According to the present invention relating to the "third invention group", the deterioration state of the lubricant due to the oxidative deterioration of the lubricant, the contamination by foreign matters, or the like can be easily and accurately detected in a short time. In addition, since the required amount of the lubricant is very small, for example, about 10 mg, it is possible to analyze the lubricant in a portion directly affecting the life of the lubricated portion, for example, in the vicinity of the raceway of the bearing, in addition to the absence of deterioration of the detection device and the need for cleaning, and it is possible to improve the accuracy of failure prediction. Further, the grease can be detected in addition to the lubricating oil, and the grease can be detected in various places without limitation of the light source.

DESCRIPTION OF EMBODIMENTS

Figure 1:
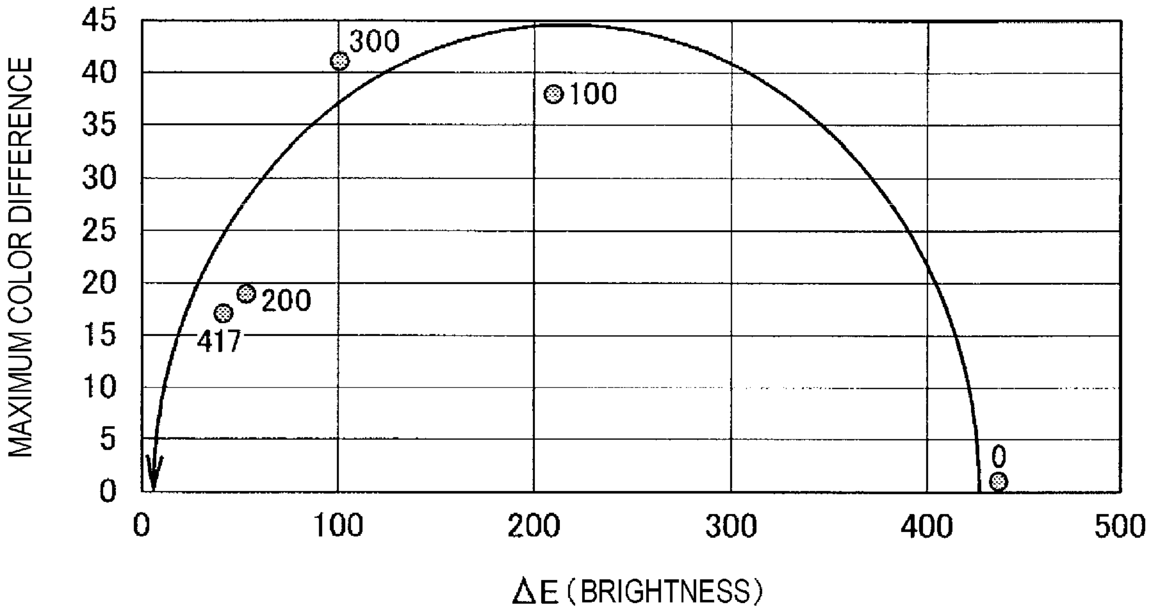
FIG. 1 is a graph showing a result of analyzing grease in a vicinity of a cage of a rolling bearing by a grease deterioration detecting method according to a first embodiment of the present invention.

Embodiments of the present invention will be described below. The present embodiment is an example of the present invention, and the present invention is not limited to the present embodiment. In addition, various modifications or improvements can be added to the present embodiment, and such modifications or improvements can also be included in the present invention.

In the following embodiments, an embodiment for describing the present invention according to the "first invention group" is referred to as a "first embodiment", an embodiment for describing the present invention according to the "second invention group" is referred to as a "second embodiment", and an embodiment for describing the present invention according to the "third invention group" is referred to as a "third embodiment".

First Embodiment

First, the first embodiment will be described.

The grease deterioration detecting method according to the present embodiment is a method for detecting deterioration of grease, and includes a dilution step of diluting grease with a diluent to obtain diluted grease, and a measurement step of measuring a color of the diluted grease with a sensor.

According to the grease deterioration detecting method of the present embodiment, the deterioration of the grease can be detected by measuring the color of the diluted grease with the sensor. That is, since the color changes when the grease deteriorates, whether the grease has deteriorated due to use or storage can be determined by measuring the color of the grease with a sensor.

Specific contents of the deterioration of the grease that can be detected include, for example, oxidation of the grease and contamination of the grease by foreign matters. A specific example of the sensor used for measurement is a color sensor.

Further, according to the grease deterioration detecting method of the present embodiment, the deterioration state and the degree of deterioration of the grease can be determined by measuring the color of the diluted grease with the sensor. That is, since the degree of color change increases as the deterioration of grease progresses, the degree of deterioration of grease due to use or storage can be determined by measuring the color of grease with a sensor.

For example, the deterioration state and the degree of deterioration of the grease can be determined by comparing a color of grease for which the degree of deterioration is to be determined with a color of reference grease. More specifically, non-deteriorated grease such as unused grease and grease immediately after production is used as reference grease, the reference grease is diluted with a diluent to obtain diluted reference grease, and a color of the diluted reference grease is measured by a sensor (reference grease measurement step).

Next, grease as a sample for which the degree of deterioration is to be determined is diluted with a diluent to obtain diluted grease (dilution step), and a color of the diluted grease is measured with a sensor (measurement step). Then, the degree of deterioration of the grease is determined by comparing the color of the diluted reference grease obtained in the reference grease measurement step with the color of the diluted grease obtained in the measurement step (comparison step). It is preferable that the type of the diluent and the measurement condition of the color are the same between the reference grease and the grease as the sample.

Accordingly, when the grease deterioration detecting method according to the present embodiment is used, the degree of deterioration of grease used for, for example, a rolling bearing can be determined. When the degree of deterioration of the grease is known, the timing of maintenance such as replenishment of a rolling bearing with unused grease or replacement of a rolling bearing can be appropriately determined.

In the grease deterioration detecting method according to the present embodiment, the color of diluted grease obtained by diluting grease with a diluent is measured, so that a small amount (for example, 10 mg) of grease is sufficient for detecting deterioration. Even with a small amount of grease, both deterioration due to oxidation and deterioration due to foreign matter contamination can be detected in a short time.

Further, in the grease deterioration detecting method according to the present embodiment, a small amount of grease is sufficient for detecting deterioration, so that grease existing in a vicinity of a raceway directly affecting the life of the rolling bearing can be analyzed. Accordingly, the determination of the degree of deterioration of grease used for the rolling bearing and the prediction of failure of the rolling bearing can be performed with high accuracy.

The conditions for diluting the grease with the diluent are not particularly limited. The temperature may be room temperature, or heating may be performed as long as the diluent does not volatilize. In addition, stirring may or may not be performed during dilution.

In addition, a dilution ratio when the grease is diluted with the diluent is not particularly limited, and in order to perform color measurement with high accuracy, it is preferable to mix 1 part by mass or more and 10000 parts by mass or less of the diluent with 1 part by mass of the grease and dilute the grease, it is more preferable to mix 10 parts by mass or more and 10000 parts by mass or less of the diluent with 1 part by mass of the grease and dilute the grease, and it is still more preferable to mix 10 parts by mass or more and 1000 parts by mass or less of the diluent with 1 part by mass of the grease and dilute the grease.

The type of the diluent is not particularly limited as long as the diluent is easily mixed with the grease and has the degree of colorless and transparency that does not cause any problem when measuring the color of the diluted grease with a sensor, and an organic solvent is suitable. The diluent may be used alone or in combination of two or more kinds thereof.

Specific examples of the organic solvent include: petroleum such as kerosene, diesel fuel, and gasoline; alcohols such as methanol and ethanol; ketone-based solvents such as acetone and methyl ethyl ketone; aliphatic hydrocarbon such as n-hexane and cyclohexane; aromatic hydrocarbon such as toluene and xylene; halogenated hydrocarbon such as chloroform and monochlorobenzene; ester-based solvents such as ethyl acetate; and ether-based solvents such as tetrahydrofuran.

Examples According to First Embodiment

An example of monitoring the degree of deterioration of lubricating grease used for a rolling bearing will be described. The rolling bearing used was a deep groove ball bearing of nominal number 6305 VV having an inner diameter of 25 mm, an outer diameter of 62 mm, and a width of 17 mm. The thickener of the grease used is lithium soap, and the base oil is a mixture of poly-α-olefin and diester oil (the dynamic viscosity at 40° C. is 15.9 $mm^2/s$), and the consistency is No. 2.

The grease was loaded into the rolling bearing, and an inner ring was rotated at a rotational speed of 10000 $min^{-1}$ while applying a radial load of 98 N and an axial load of 1470 N. The outer ring temperature was set to 140° C. The rotation time was set to 100 hours, 200 hours, 300 hours, and 417 hours. After the rotation for each time, grease was collected from the rolling bearing. The grease is collected at three positions, that is, a portion in a vicinity of the cage of the rolling bearing, a portion in a vicinity of and inside the seal, and a portion in a vicinity of and outside the seal. It should be noted that the rotation time of 417 hours is that the rotation was stopped because the outer ring temperature increased to 170° C.

Each of 10 mg of the collected grease was dissolved in 1 mL of n-hexane to obtain diluted grease. Then, the hue of each diluted grease was measured by using an oil diagnostic meter T-ODS-301 manufactured by MKT Taisei Co., Ltd. The hue is expressed by three colors that are red (R), green (G), and blue (B), and is expressed by 256 gradations of colors 0 to 255. The brightness ΔE of each diluted grease was calculated by substituting the RGB values obtained by the color sensor into the following formula.

$$\Delta E = (R^2 + G^2 + B^2)^{0.5}$$

In addition, the difference between the maximum value and the minimum value of the RGB values obtained by the color sensor was determined, and this was defined as the maximum color difference of each diluted grease.

Figure 2:
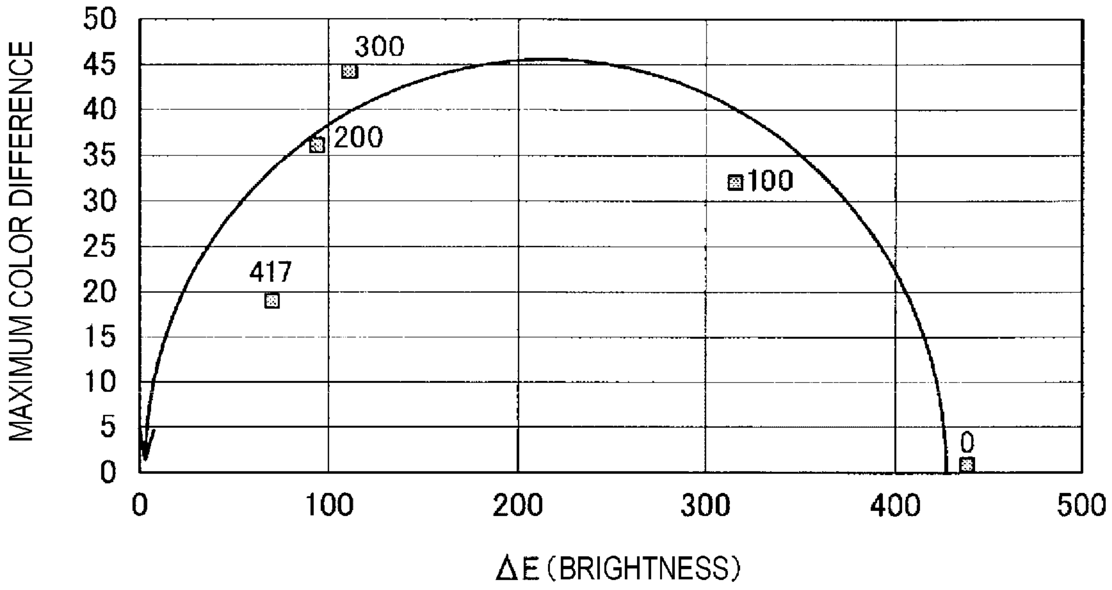
FIG. 2 is a graph showing a result of analyzing grease inside a seal of a rolling bearing by the grease deterioration detecting method according to the first embodiment of the present invention.
Figure 3:
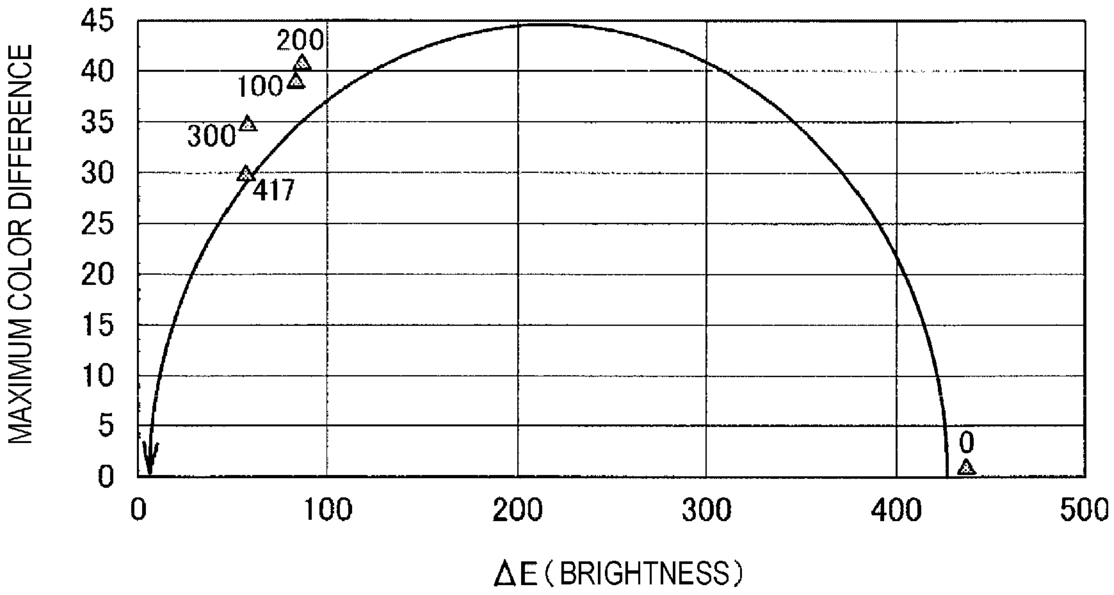
FIG. 3 is a graph showing a result of analyzing grease outside the seal of the rolling bearing by the grease deterioration detecting method according to the first embodiment of the present invention.

A graph in which the brightness ΔE and the maximum color difference are plotted for each grease collection position is shown in FIGS. 1 to 3. The collection position in the graph of FIG. 1 is a portion in the vicinity of the cage, the collection position in the graph of FIG. 2 is the inner portion of the seal, and the collection position in the graph of FIG. 3 is the outer portion of the seal. In addition, a numerical value written in the vicinity of a plot in the graph is a rotation time of the rolling bearing. The rotation time of 0 hour is for the unused grease, and the hue was measured in the same manner as in the grease of each rotation time using the unused grease as a reference grease.

As the rotation time of the rolling bearing increases, the degree of deterioration of the grease increases, and as the degree of deterioration of the grease increases, the hue of the grease changes, the maximum color difference increases, and the brightness ΔE decreases. That is, the color of the grease changes from colorless (white) to black. When the brightness ΔE and the maximum color difference are plotted, a curve as shown in the graph is drawn by an arrow curved in a substantially semicircular shape.

The brightness ΔE of the unused grease is about 442 (R=255, G=255, B=255), but the brightness ΔE approaches 0 as the degree of deterioration of the grease increases. This may indicate that solid particles such as abrasion powder are mixed in grease as foreign matters.

The graphs of FIGS. 1 to 3 will be described. The unused grease is almost colorless and has a large brightness ΔE, and as the rotation time increases, the color of the grease becomes brown, so that the brightness ΔE decreases. As the blue decreases, the maximum color difference increases. When the rotation time further increases, the color of the grease becomes closer to black (R=0, G=0, B=0) as the rolling bearing becomes closer to burning. Therefore, a result was obtained that the brightness ΔE further decreased and the maximum color difference decreased.

In this way, when the brightness ΔE and the maximum color difference are plotted, a curve as shown in the graph is drawn by an arrow curved in a substantially semicircular shape, and thus the degree of deterioration of the grease can be determined by checking where on the curve the brightness ΔE and the maximum color difference of the diluted grease are plotted are located.

Second Embodiment

Next, the second embodiment will be described.

The grease deterioration detecting method according to the present embodiment includes a step of forming a thin film by sandwiching the grease between a pair of transparent material plates and spreading the grease, and a step of measuring the color of the thin film grease with a camera or a sensor. The degree of deterioration of the grease is determined by the measurement step.

In addition, steps other than the above steps may be included as long as the effects of the present invention are not impaired.

(Thin Film Forming Step)

When the grease deteriorates, the color changes. However, grease has lower fluidity and higher viscosity than lubricating oil. Therefore, the light transmittance is also low, and it is difficult to determine a minute difference in deterioration even if determination can be performed in a case in which a difference in hue is large, such as an initial state in which deterioration does not occur at all, and a state in which deterioration progresses considerably.

In contrast, the present embodiment includes a step of forming a thin film by sandwiching the grease between a pair of plates made of a transparent material and spreading the grease. As a result, the light transmittance of the grease is increased, and a minute difference in deterioration can be clearly determined as a difference in hue.

Further, in order to spread the grease to form a thin film, a small amount of grease is sufficient. Therefore, the accuracy of failure prediction is increased, for example, the grease in a portion directly affecting the life of the component to which the grease adheres is analyzed at a pinpoint. Specifically, in a case in which the component is a rolling bearing, grease existing in the vicinity of the raceway is analyzed, and determination of the degree of deterioration of grease used for the rolling bearing and prediction of failure of the rolling bearing can be performed with high accuracy.

The pair of transparent materials is not particularly limited as long as the grease can form a thin film by sandwiching and spreading the grease therebetween and the observation of the hue of the grease is not affected.

For example, at least one selected from the group consisting of glass, acryl, polyethylene terephthalate, and polycarbonate are preferred, and among these materials, the same transparent material may be used as a pair of transparent materials, or two different materials may be used as a pair of transparent materials.

The plate made of the transparent material may have flat surfaces for sandwiching the grease, and the size and thickness of the plate are not particularly limited. The preferred range of the size and thickness of the plate varies depending on the transparent material to be used, the spreading method, the amount of grease, and the like. For example, in a case in which two glass slides are used as a pair of transparent materials and grease is spread by applying a human force on the slide glasses, the strength and thickness of the glass may be set to such a degree that the glass is not broken by the force. Further, the transparent material may have such a size that the thin grease does not jump out when the grease is spread. Further, the size and thickness of the pair of plates made of a transparent material are not necessarily the same.

The amount of grease sandwiched between the pair of plates made of a transparent material, that is, the amount of grease necessary for the grease deterioration detecting method according to the present embodiment varies depending on the size of the transparent material to be used and the hardness of the grease, and is preferably 0.1 mg or more, more preferably 0.2 mg or more, and still more preferably 0.5 mg or more, from the viewpoint of easily detecting the thickness and area of the grease when the grease is spread. In addition, from the viewpoint of analyzing, at a pinpoint, grease in a portion directly affecting the life of the component, the amount of grease is preferably 10 mg or less, more preferably 5 mg or less, and still more preferably 2 mg or less.

The size of the grease after being spread is preferably 1.5 mm or more in diameter, more preferably 3 mm or more in diameter, and still more preferably 5 mm or more in diameter, from the viewpoint of ease of visual recognition during detection. From the viewpoint of ease of handling, the size of the grease after being spread is preferably 30 mm or less in diameter, and more preferably 15 mm or less in diameter. Note that the above size does not mean that the grease after being spread has an accurate circular shape. That is, it is sufficient that an area of the grease after being spread is substantially equal to an area of the circle having the above diameter.

The thickness of the grease after being spread is preferably 10 μm or more, and more preferably 20 μm or more, from the viewpoint of improving the accuracy of the hue analysis. From the viewpoint of preventing the light transmittance from becoming too low, the thickness of the grease after being spread is preferably 0.5 mm or less, and more preferably 0.1 mm or less. However, when a foreign matter such as iron powder is contained in the grease, the thickness may vary depending on the size of the iron powder.

The thickness of the grease after being spread can be calculated based on the amount, specific gravity, and area of the grease used. The thickness of the grease after being spread may also be directly measured using dielectric constant measurement.

The method for collecting grease from components is not particularly limited, and examples thereof include a method for directly collecting grease from a bearing or the like using a spatula, and a method for collecting grease coming out from a grease discharge port.

When the grease is formed into a thin film, the diluent is not particularly required, but the use of the diluent is not excluded.

For example, in a case in which the grease is solidified, for example, due to the deterioration of the grease being very advanced, and it is difficult to form the grease into a thin film even when the grease is sandwiched between a pair of plates made of a transparent material and is spread, the viscosity of the grease may be reduced using a diluent, and then the grease may be formed into a thin film. In addition, even in a case in which the deterioration of the grease progresses very much and the color is too dark to determine the degree of the further deterioration, the color of the grease may be made lighter by using the diluent so as to facilitate the determination.

The dilution ratio for diluting the grease with the diluent is not particularly limited, and is appropriately determined according to the state of the grease.

The diluent is not particularly limited as long as it is easily mixed with grease and has such a degree of colorless and transparency that does not cause a problem when measuring the color of grease with a camera or a sensor, and an organic solvent is suitable. The diluent may be used alone or in combination of two or more kinds thereof.

Specific examples of the organic solvent include: petroleum such as kerosene, diesel fuel, and gasoline; alcohols such as methanol and ethanol; ketone-based solvents such as acetone and methyl ethyl ketone; aliphatic hydrocarbon such as n-hexane and cyclohexane; aromatic hydrocarbon such as toluene and xylene; halogenated hydrocarbon such as chloroform and monochlorobenzene; ester-based solvents such as ethyl acetate; and ether-based solvents such as tetrahydrofuran.

(Measurement Step)

Next, a step of measuring the color of the thin-film grease with a camera or a sensor is performed. The degree of deterioration of the grease is determined by this measurement.

Specific contents of the deterioration of the grease that can be detected include, for example, oxidation of the grease, a component change due to heat of the grease, and contamination of the grease by foreign matters such as iron powder.

The sensor used for measurement is preferred because the color sensor can directly determine the color of grease.

The degree of color changes of grease increases as deterioration progresses. Therefore, the degree of deterioration of the grease can be determined by measuring the color of the grease with a sensor such as a color sensor.

In particular, in the grease deterioration detecting method according to the present embodiment, the grease is formed into a thin film, so that the light transmittance of the grease is increased, and a minute difference in deterioration can be clearly determined as a difference in hue. Therefore, the degree of deterioration of the grease can be detected in detail.

In one embodiment, the degree of deterioration of the grease is determined by comparing the color of the thin-film grease with the color of the reference grease. Specifically, grease that is not deteriorated, such as unused grease or grease immediately after production, is used as "reference grease", and the reference grease is sandwiched between a pair of plates made of a transparent material and is spread to form a thin film. In this case, it is preferable that the amount of the reference grease and the area and the thickness of the reference grease after being spread are the same as the amount of grease whose degree of deterioration is to be detected, and the area and the thickness of the grease after being spread. The color of the reference grease is measured by a sensor and used as a reference for the following measurement.

Next, a color of the thin-film grease, which is obtained by sandwiching the grease whose degree of deterioration is to be detected between a pair of transparent materials and spreading the grease as described above, is measured by a sensor. Then, the degree of deterioration of the grease is determined by comparison with the color of the reference grease.

In the case in which the color of the grease is measured by a camera instead of the sensor, the degree of deterioration of the grease is also determined by comparing the color of the grease with the color of the reference grease as described above.

The thin-film grease, which is obtained by sandwiching the grease whose degree of deterioration is to be detected between a pair of transparent materials and spreading the grease, is imaged together with, for example, a color chart in a state in which a white object is placed on the background. The color chart is used for the standardization of colors, and this makes it possible to correct white balance or the like for an image after imaging, and to determine the degree of deterioration regardless of conditions such as brightness of a place where the imaging is performed.

The thin-film grease, which is obtained by sandwiching the reference grease between a pair of transparent materials and spreading the reference grease, may be imaged and corrected, together with the grease whose degree of deterioration is to be detected, in a state in which a white object is placed on the background, or may be imaged with the color chart in advance and brought into a state in which the white balance or the like has been corrected, and may be compared with a color of grease whose degree of deterioration is to be detected and which is imaged and corrected actually.

The degree of deterioration is determined based on the brightness of the color of the thin-film grease that is measured by the camera or the sensor.

The hue is expressed by three colors that are red (R), green (G), and blue (B), and is expressed by 256 gradations of colors 0 to 255. The brightness ΔE of the grease is calculated by substituting the RGB values obtained by the sensor or the RGB values extracted from the hue information of the image captured and corrected by the camera into the following formula.

$$\Delta E = (R^2 + G^2 + B^2)^{0.5}$$

Further, a difference between the maximum value and the minimum value of the RGB values obtained by measurement with a camera or a sensor is defined as the maximum color difference of each grease.

Regarding the reference grease and the grease whose degree of deterioration is to be detected, the above brightness ΔE and the maximum color difference are determined, and the brightness ΔE is plotted on the X-axis and the maximum color difference is plotted on the Y-axis, so that the degree of deterioration of the grease can be determined.

In this way, by using the grease deterioration detecting method according to the present embodiment, the degree of deterioration of grease used for, for example, a rolling bearing or the like can be determined by narrowing down the place. When the degree of deterioration at each place where the grease is applied is known, it is also possible to take measures such as appropriately determining the period of maintenance such as replenishment of the rolling bearing with unused grease or replacement of the rolling bearing, and changing the maintenance period at each place.

In addition, in the grease deterioration detecting method according to the present embodiment, a small amount of grease is sufficient for detecting deterioration, and detection can be performed in a short time. Therefore, the degree of deterioration of grease collected from a component such as a rolling bearing can be determined very easily and accurately on the spot.

Furthermore, not only deterioration due to foreign matter contamination but also deterioration due to oxidation and deterioration due to a component change due to heat can be detected, which is very useful.

Examples According to Second Embodiment

Examples 1 to 7

The degree of deterioration of lubricating grease used for a rolling bearing was monitored.

A rolling bearing having an inner diameter of 25 mm, an outer diameter of 62 mm, and a width of 17 mm was used, grease was loaded into the rolling bearing, and the rolling bearing was continuously rotated under the conditions of a rotational speed of 2000 r/min, a bearing outer ring temperature of 120° C., a radial load of 98 N, and an axial load of 1470 N. Commercially available grease in which the thickener of the grease used was lithium soap, the consistency was No. 2, and the base oil was mineral oil was used.

The test time was set to 0 to 600 hours as described in Table 1, and after rotating at each time, grease was collected from the outside of the seal of the rolling bearing using a spatula. In the example in which the rotation time was 600 hours, the rotation was stopped after the elapse of time, and the subsequent restart was not possible due to an increase in bearing torque.

1 mg of the collected grease was sandwiched between a pair of slide glasses and spread by applying a force, so that a thin film having a diameter of 6 mm and a thickness of about 40 μm was obtained. Next, the grease which was formed into a thin film was imaged by a camera, and hue information was extracted from the image data. At this time, white balance correction was performed by imaging grease together with a color chart. The hue is expressed by three colors that are red (R), green (G), and blue (B), and is expressed by 256 gradations of colors 0 to 255. The brightness ΔE of each grease was determined by substituting the RGB values into the following formula. The maximum color difference, which was the difference between the maximum value and the minimum value of the RGB values, was also determined.

$$\Delta E = (R^2 + G^2 + B^2)^{0.5}$$

Figure 4:
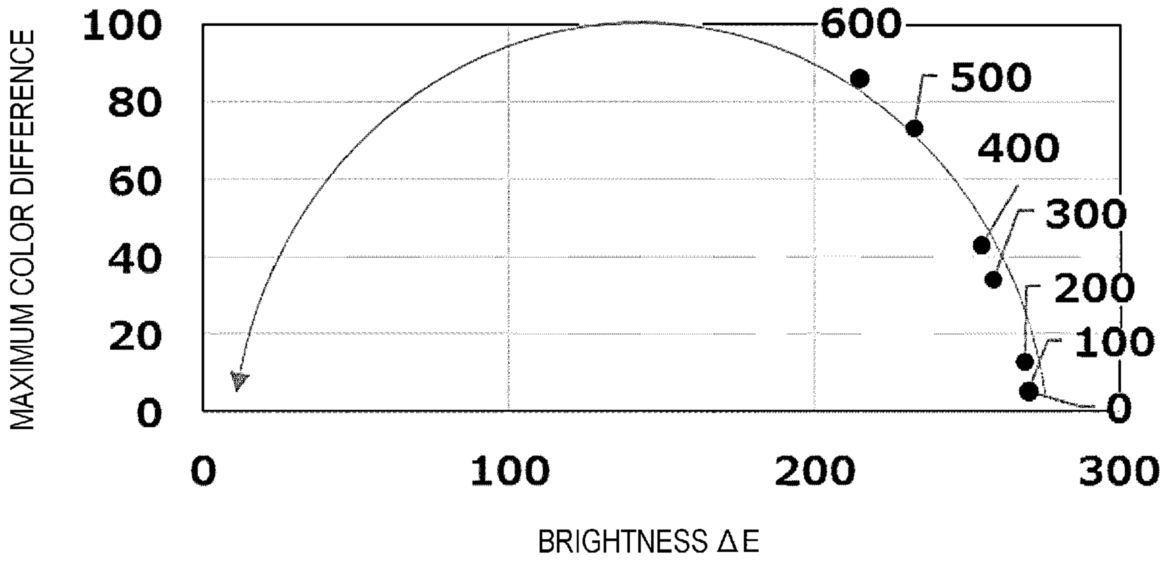
FIG. 4 is a graph showing a relationship between the brightness ΔE and the maximum color difference obtained in an example using a grease deterioration detecting method according to a second embodiment of the present invention.

The results are shown in Table 1 and FIG. 4. Numbers described in a vicinity of the plots in FIG. 4 indicate rotation times.

TABLE 1

| | Rotation time (hr) | R | G | B | Brightness ΔE | Maximum color difference |
|---|---|---|---|---|---|---|
| Example 1 | 0 | 156 | 154 | 159 | 271 | 5 |
| Example 2 | 100 | 158 | 153 | 157 | 270 | 5 |
| Example 3 | 200 | 162 | 155 | 149 | 269 | 13 |
| Example 4 | 300 | 164 | 152 | 130 | 259 | 34 |
| Example 5 | 400 | 165 | 151 | 122 | 255 | 43 |
| Example 6 | 500 | 163 | 140 | 90 | 233 | 73 |
| Example 7 | 600 | 158 | 127 | 72 | 215 | 86 |

As a result, in Example 1, which can be referred to as reference grease, there was almost no color and the brightness ΔE was high. In contrast, as the rotation time elapsed, the grease deteriorated and turned brown. Specifically, since the brightness ΔE decreased and the blue (B) value decreased in the hue, a continuous change in which the maximum color difference increased was observed.

The degree of deterioration of the grease can be determined by which position of the substantially semicircular shape shown in FIG. 4 the brightness ΔE and the maximum color difference are located.

As the degree of deterioration of the grease increases, the color of the grease changes from colorless (white) to brown. That is, the brightness ΔE of the grease decreases and the blue (B) value decreases when the grease is brown, so that the maximum color difference increases. Then, the rotation time further increases, the degree of deterioration increases as the rolling bearing becomes closer to burning, and the color of the grease changes from brown to black (R=0, G=0, B=0). Therefore, the brightness ΔE further decreases, and the maximum color difference also decreases.

Such a change is shown by drawing a curve as shown in the graph with an arrow curved in a substantially semicircular shape. In a case in which the brightness ΔE is in a region close to 0, there is also a possibility that not only deterioration due to oxidation of the grease but also solid particles such as abrasion powder are mixed in the grease as a foreign matter.

In Examples 1 to 7, since the grease outside the seal of the rolling bearing is subjected to the deterioration detection, the change in the hue is smaller than that of the grease actually applied to the portion contributing to lubrication, but as the threshold value, it is preferable to re-apply the grease or replace the rolling bearing when the brightness of the grease reaches about half of the brightness ΔE of the new grease with the rotation time of 0 as the reference grease.

In the case in which the grease deterioration detecting method according to the present embodiment is actually used, it is preferred since the degree of deterioration of the grease can be determined at first glance when the brightness ΔE and the maximum color difference are plotted as shown in FIG. 4, and the position of the brightness ΔE and the maximum color difference located on a curve such as an arrow curved in a substantially semicircular shape is observed.

Third Embodiment

First, the third embodiment will be described.

In the lubricant deterioration detecting method (hereinafter, referred to as "deterioration detecting method") according to the present invention, first, a device or equipment using a lubricating oil or grease (hereinafter, collectively referred to as "lubricant"), for example, a rolling bearing or a ball screw device is stopped, the lubricant is collected and taken into a container, and the lubricant is imaged together with a color chart. Various types of imaging devices can be used for imaging, and the types of the imaging devices are not particularly limited, and the imaging can be performed using, for example, a camera-equipped portable terminal such as digital cameras, smartphones, and tablets. The type of a light source during imaging is not particularly limited, and detection can be performed at various places.

Figure 5:
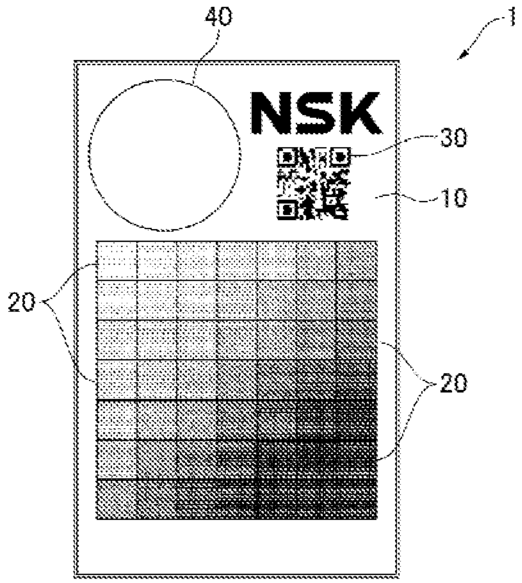
FIG. 5 is a top view illustrating an example of a color chart used in a third embodiment of the present invention.

As shown in FIG. 5, a color chart 1 is a list in which a plurality of color samples 20 different in hue and shade from white (upper left in the drawing) to black (lower right in the drawing) are arranged on a surface of a mount 10. The image information of the color chart 1 is printed on the mount 10 as an identification code 30. As the identification code 30, a bar code, a QR code (registered trademark) shown in the figure, or the like is used.

Then, the collected lubricant is charged into a container (not shown) such as a petri dish or a transparent bottle, the container is placed on a sample placement portion 40 indicated by a circle in the figure, and the collected lubricant is imaged together with the color chart 1 using various imaging devices. Here, the amount of the collected lubricant is sufficient to be about 10 mg, which is a very small amount. The lubricant may be used alone or may be diluted with a solvent. The solvent is not particularly limited as long as it is easily mixed with the lubricant and has a degree of colorless and transparency that does not interfere with imaging of the color of the lubricant, and specifically, organic solvents, kerosene compounds, and gasoline compounds are preferred. By diluting the lubricant with a solvent, the lubricant that is discolored to a dark color, particularly to a black color can be more finely separated.

The image information of the imaged lubricant is compared with the image information of the color chart 1. At this time, it is preferable to correct the white balance included in the image information of the imaged lubricant. By correcting the white balance, the image information of the imaged lubricant can be made more appropriately conform to the image information of the color chart 1 regardless of the environment of the imaging place, that is, the detection place, which may be affected by brightness or the like.

In the case in which the imaging device to be used has a white balance correction function, the white balance correction can be performed by the white balance correction function of the imaging device, and image information obtained by an imaging device may be transmitted to an external processing device such as a server, and correction may be performed by a white balance correction function provided in the processing device. In addition, the comparison between the image information of the lubricant and the image information of the color chart 1, which will be described later, may be performed in the imaging device, or may be performed in an external processing device.

Next, a hue of an image of the lubricant whose white balance has been corrected (hereinafter referred to as a "corrected image") is determined. The hue is expressed by three colors of red (R), green (G), and blue (B), and the brightness (ΔE) is determined from the following formula (1) based on the RGB values of the corrected image.

$$\text{Brightness } (\Delta E) = (R^2 + G^2 + B^2)^{0.5} \quad (1)$$

The difference between the maximum value and the minimum value of the RGB values is defined as the maximum color difference of the lubricant corrected image.

Then, as shown in a test example to be described later, the lubricant is collected every predetermined use time, the brightness (ΔE) and the maximum color difference are determined, and when the brightness (ΔE) is plotted on the X-axis and the maximum color difference is plotted on the Y-axis to form a graph, a correlation is obtained. Based on the graph, the degree of deterioration (deterioration state) of the collected lubricant can be determined. The degree of deterioration can be reflected in the replacement period of the lubricant or the like.

The correction according to the dilution ratio can be performed by a correction table or the like prepared in advance by providing a correction function in the imaging device or the server.

Examples According to Third Embodiment

Hereinafter, an example in which the deterioration state of grease of a rolling bearing is monitored is shown as Test Example 1, and an example in which the deterioration state of lubricating oil of a rolling bearing is monitored is shown as Test Example 2.

Test Example 1: Example in which Deterioration State of Grease of Rolling Bearing is Monitored A rolling bearing having an inner diameter of 25 mm, an outer diameter of 62 mm, and a width of 17 mm was continuously rotated under the following conditions: rotation of an inner ring, lubrication caused by grease, rotational speed: 2000 r/min, bearing outer ring temperature: 120° C., radial load: 98 N, and an axial load: 1470 N. In addition, as grease, commercially available grease in which the base oil was mineral oil, the thickener was lithium soap, and the consistency was No. 2 was used.

Then, grease was collected from each of the rolling bearings operated for 100 hours, 200 hours, 300 hours, 400 hours, 500 hours, and 600 hours. Regarding the rolling bearing that was operated for 600 hours, the operation was stopped, grease was collected, and then the restart of operation was attempted, but the operation could not be restarted due to an increase in the bearing torque.

The grease was collected in an amount of 10 mg and dissolved in 1 mL of hexane.

Each of the collected greases was charged in a petri dish and placed on a sample placement portion of a color chart, the grease and the color chart were together imaged with a digital camera having a white balance correction function, and RGB values were determined from the obtained corrected image. The results of calculating the brightness (ΔE) and the maximum color difference from the obtained RGB values are shown in Table 2 below.

TABLE 2

| Elapsed time (hr) | R | G | B | Brightness ΔE | Maximum color difference |
|---|---|---|---|---|---|
| 0 | 137 | 138 | 143 | 241 | 6 |
| 100 | 146 | 144 | 149 | 253 | 5 |
| 200 | 152 | 141 | 123 | 241 | 29 |
| 300 | 153 | 134 | 101 | 227 | 52 |
| 400 | 150 | 125 | 84 | 213 | 66 |
| 500 | 147 | 115 | 64 | 197 | 83 |
| 600 | 134 | 97 | 42 | 171 | 92 |

Figure 6:
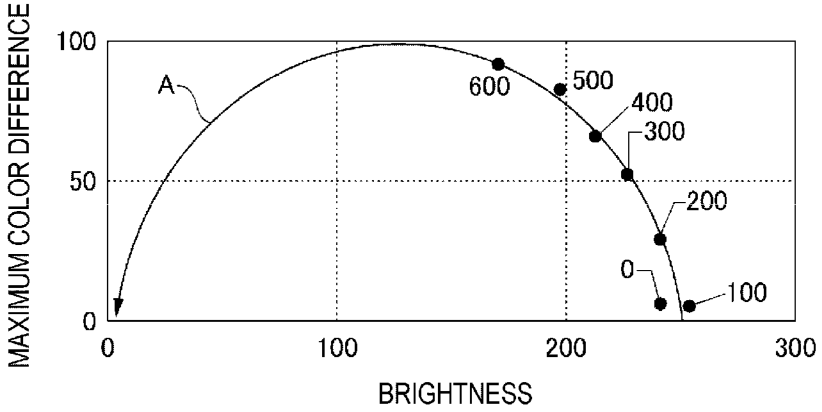
FIG. 6 is a graph showing the results of Test Example 1 in the third embodiment of the present invention.

FIG. 6 shows the result of plotting the brightness (ΔE) on the X-axis and the maximum color difference on the Y-axis. Numbers in the figure indicate respective operation times (hr). As a result, new products have almost no color and high brightness. However, as the operation time elapsed, the grease deteriorated and turned brown, so that the brightness decreased, the blue color decreased, the maximum color difference increased, and a continuous change along a curve A indicated by a substantially semicircular arrow in the figure was observed.

Therefore, the collected grease is imaged together with the color chart, the brightness (ΔE) and the maximum color difference of the corrected image are determined, and the degree of deterioration of the collected grease can be determined by where on the curve A shown in FIG. 6 the brightness (ΔE) and the maximum color difference are located.

Test Example 2: Example in which Deterioration State of Lubricating Oil of Rolling Bearing is Monitored A thrust cylindrical roller bearing having an inner diameter of 60 mm, an outer diameter of 95 mm, and a nominal height of 26 mm was continuously rotated under the following conditions: rotation of the inner ring, lubrication with lubricating oil, rotational speed: 500 r/min, bearing temperature: 100° C., and axial load: 60 kN. As the lubricating oil, lubricating oil equivalent to VG 32 was used, and the oil was supplied under the condition of 0.1 L/min.

After the thrust cylindrical roller bearing was operated for 515 hours, 800 hours, and 1136 hours, lubricating oil was collected from an oil collection tank.

The amount of the lubricating oil collected was set to 1 mL, followed by charging the lubricating oil in a petri dish without being diluted and placing the petri dish on the sample placement portion of the color chart, each lubricating oil and the color chart were imaged together with a digital camera having a white balance correction function, and RGB values were determined from the obtained corrected image. The results of calculating the brightness (ΔE) and the maximum color difference from the determined RGB values are shown in Table 3 below.

TABLE 3

| Elapsed time (hr) | R | G | B | Brightness ΔE | Maximum color difference |
|---|---|---|---|---|---|
| 0 | 255 | 255 | 255 | 442 | 0 |
| 515 | 237 | 232 | 194 | 384 | 43 |
| 800 | 223 | 204 | 185 | 355 | 38 |
| 1136 | 221 | 190 | 134 | 321 | 87 |

Figure 7:
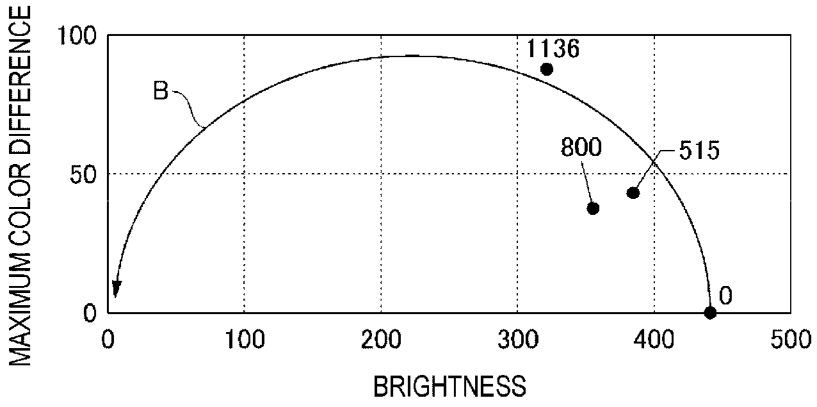
FIG. 7 is a graph showing the results of Test Example 2 in the third embodiment of the present invention.

FIG. 7 shows the result of plotting the brightness (ΔE) on the X-axis and the maximum color difference on the Y-axis. Numbers in the figure indicate respective operation times (hr). As a result, new products have almost no color and high brightness. However, as the operation time elapsed, the grease deteriorated and turned brown, so that the brightness decreased, the blue color decreased, the maximum color difference increased, and a continuous change along a curve B indicated by a substantially semicircular arrow in the figure was observed.

Therefore, the collected lubricating oil is imaged together with the color chart, the brightness (ΔE) of the corrected image and the maximum color difference are determined, and the degree of deterioration of the collected lubricating oil can be determined by where on the curve B shown in FIG. 7 the brightness (ΔE) and the maximum color difference are located.

Although the embodiments are described above with reference to the drawings, it is needless to say that the present invention is not limited to such examples. It will be apparent to those skilled in the art that various changes and modifications may be conceived within the scope of the claims, and it is also understood that the various changes and modifications belong to the technical scope of the present invention. Components in the embodiments described above may be combined freely within a range not departing from the spirit of the present invention.

The present application is based on Japanese Patent Application No. 2021-093548 filed on Jun. 3, 2021, Japanese Patent Application No. 2022-025090 filed on Feb. 21, 2022, Japanese Design Registration Application No. 2022-004481 filed on Mar. 4, 2022, and Japanese Patent Application No. 2022-086825 filed on May 27, 2022, the contents of which are incorporated herein by reference.

REFERENCE SIGNS LIST

1 color chart
10 mount
20 color sample
30 identification code
40 sample placement portion

The invention claimed is:

1. A grease deterioration detecting method, which is a method for detecting deterioration of grease, the method comprising:

a dilution step of diluting grease with a diluent to obtain diluted grease, the dilution step comprising collecting the grease from three portions of a rolling bearing, the three portions comprising a first portion in a vicinity of a cage of the rolling bearing, a second portion in a vicinity of and inside a seal of the rolling bearing, and a third portion in a vicinity of and outside the seal; and a measurement step of measuring a color of the diluted grease with a sensor.

2. The grease deterioration detecting method according to claim 1, wherein the sensor is a color sensor.

3. The grease deterioration detecting method according to claim 1, wherein the diluent is an organic solvent.

4. The grease deterioration detecting method according to claim 3, wherein the organic solvent is at least one selected from the group consisting of n-hexane, kerosene, and gasoline.

5. A grease deterioration detecting method, which is a method for detecting deterioration of grease, the method comprising:

a step of forming a thin film by sandwiching grease between a pair of plates made of a transparent material and spreading the grease;

a step of collecting the grease from three portions of a rolling bearing, the three portions comprising a first portion in a vicinity of a cage of the rolling bearing, a second portion in a vicinity of and inside a seal of the rolling bearing, and a third portion in a vicinity of and outside the seal; and a step of measuring a color of the thin-film grease with a camera or a sensor, in which a degree of deterioration of the grease is determined by the measurement.

6. The grease deterioration detecting method according to claim 5, wherein the sensor is a color sensor.

7. The grease deterioration detecting method according to claim 5, wherein the transparent material is at least one selected from the group consisting of glass, acryl, polyethylene terephthalate, and polycarbonate.

8. A lubricant deterioration detecting method comprising:

a step of collecting a lubricant or a lubricant diluted with a solvent from three portions of a rolling bearing, the three portions comprising a first portion in a vicinity of a cage of the rolling bearing, a second portion in a vicinity of and inside a seal of the rolling bearing, and a third portion in a vicinity of and outside the seal;

a step of imaging only the lubricant or the lubricant diluted with the solvent together with a color chart using an imaging device; and a step of determining a deterioration state of the lubricant from image information of only the imaged lubricant or the imaged lubricant diluted with the solvent based on image information of the imaged color chart.

9. The lubricant deterioration detecting method according to claim 8, wherein white balance of the image information of only the imaged lubricant or the imaged lubricant diluted with the solvent is corrected based on white balance of the image information of the color chart, and a deterioration state of the lubricant is determined based on the corrected image information.

10. The lubricant deterioration detecting method according to claim 8, wherein the imaging device has a white balance correction function.

11. The lubricant deterioration detecting method according to claim 10, wherein the imaging device is a digital camera or a camera-equipped portable terminal.

12. The lubricant deterioration detecting method according to claim 8, wherein the lubricant is lubricating oil or grease.

13. The lubricant deterioration detecting method according to claim 8, wherein the solvent contains an organic solvent, a kerosene compound, or a gasoline compound.

14. The lubricant deterioration detecting method according to claim 8, wherein the step of imaging only the lubricant or the lubricant diluted with the solvent together with the color chart using an imaging device comprises:

placing the lubricant or the lubricant diluted with the solvent onto the color chart; and imaging the lubricant or the lubricant diluted with the solvent and the color chart together while the lubricant or the lubricant diluted with the solvent remains placed onto the color chart.

15. The grease deterioration detecting method according to claim 1, wherein the dilution step of diluting the grease with the diluent to obtain the diluted grease comprises diluting just 10 mg of the grease with the diluent to obtain the diluted grease.

16. The grease deterioration detecting method according to claim 15, wherein the dilution step of diluting the grease with the diluent to obtain the diluted grease further comprises diluting 1 part by mass of the grease with 10 parts by mass or more and 1,000 parts by mass or less of the diluent.

17. The grease deterioration detecting method according to claim 5, wherein the step of forming the thin film by sandwiching the grease between the pair of plates made of the transparent material and spreading the grease comprises sandwiching and spreading just 0.5 mg or more and 2 mg or less of the grease between the pair of plates.

18. The grease deterioration detecting method according to claim 17, wherein the step of forming the thin film by sandwiching the grease between the pair of plates made of the transparent material and spreading the grease comprises sandwiching and spreading the 0.5 mg or more and 2 mg or less of the grease to a diameter of 5 mm or more and 15 mm or less.

19. The grease deterioration detecting method according to claim 18, wherein the step of forming the thin film by sandwiching the grease between the pair of plates made of the transparent material and spreading the grease comprises sandwiching and spreading the 0.5 mg or more and 2 mg or less of the grease to the diameter of 5 mm or more and 15 mm or less and to a thickness of 20 μm or more and 0.1 mm or less.

20. The grease deterioration detecting method according to claim 1, wherein the dilution step of diluting the grease with the diluent to obtain the diluted grease comprises diluting 1 part by mass of the grease with 10 parts by mass or more and 1,000 parts by mass or less of the diluent.

* * * * *